United States Patent
Kulprathipanja et al.

(10) Patent No.: US 7,728,187 B2
(45) Date of Patent: Jun. 1, 2010

(54) ADSORBENT AND PROCESS FOR THE SEPARATION OF META-XYLENE FROM AROMATIC HYDROCARBONS

(75) Inventors: Santi Kulprathipanja, Inverness, IL (US); Stanley J. Frey, Palatine, IL (US); Richard R Willis, Cary, IL (US); Lisa M. Knight, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 191 days.

(21) Appl. No.: 12/165,266

(22) Filed: Jun. 30, 2008

(65) Prior Publication Data

US 2009/0326310 A1    Dec. 31, 2009

(51) Int. Cl.
C07C 7/12    (2006.01)

(52) U.S. Cl. .......................... 585/828; 585/820; 585/827

(58) Field of Classification Search .................. 585/820, 585/828, 827
See application file for complete search history.

(56) References Cited

U.S. PATENT DOCUMENTS

| | | | |
|---|---|---|---|
| 3,626,020 A | 12/1971 | Neuzil | |
| 3,665,046 A | 5/1972 | De Rosset | |
| 3,668,266 A | 6/1972 | Chen et al. | |
| 3,686,342 A | 8/1972 | Neuzil | |
| 3,686,343 A | 8/1972 | Bearden, Jr. et al. | |
| 3,700,744 A | 10/1972 | Berger et al. | |
| 3,894,109 A | 7/1975 | Rosback | |
| 3,997,620 A | 12/1976 | Neuzil | |
| 4,006,197 A | 2/1977 | Bieser | |
| 4,036,745 A | 7/1977 | Broughton | |
| 4,283,587 A | 8/1981 | Rosback et al. | |
| 4,306,107 A * | 12/1981 | Broughton | 585/828 |
| 4,326,092 A | 4/1982 | Neuzil | |
| 4,368,347 A * | 1/1983 | Carra et al. | 585/828 |
| 4,442,222 A | 4/1984 | Smolin et al. | |
| 4,778,946 A | 10/1988 | Barthomeuf et al. | |
| 5,159,131 A | 10/1992 | Zinnen | |
| 5,382,747 A * | 1/1995 | Kulprathipanja | 585/828 |
| 5,849,981 A | 12/1998 | Kulprathipanja | |
| 5,900,523 A * | 5/1999 | Kulprathipanja | 585/828 |
| 5,912,395 A | 6/1999 | Noe | |
| 5,948,950 A | 9/1999 | Hotier et al. | |
| 6,207,871 B1 | 3/2001 | Hellring et al. | |
| 6,573,418 B2 * | 6/2003 | Miller et al. | 585/826 |
| 6,617,481 B1 | 9/2003 | Kulprathipanja et al. | |
| 6,706,938 B2 | 3/2004 | Roeseler et al. | |
| 6,828,470 B2 | 12/2004 | Leflaive et al. | |
| 6,838,588 B2 | 1/2005 | Leflaive et al. | |
| 2002/0143223 A1 | 10/2002 | Leflaive et al. | |
| 2003/0130556 A1 | 7/2003 | Leflaive et al. | |
| 2007/0038012 A1 * | 2/2007 | Leflaive et al. | 585/828 |
| 2007/0074800 A1 | 4/2007 | Lechtenboehmer et al. | |
| 2007/0224113 A1 * | 9/2007 | Willis et al. | 423/700 |

FOREIGN PATENT DOCUMENTS

| | | |
|---|---|---|
| EP | 1679286 (A1) | 7/2006 |
| JP | 7076531 (A) | 3/1995 |
| WO | WO2008033200 | 3/2008 |

OTHER PUBLICATIONS

Kulprathipanja, S., "Binderless Adsorbents Comprising Nano-Size Zeolite X and Their Use in the Adsorptive Separation of Para-Xylene," pending U.S. Appl. No. 12/165,329.
Cheng, Linda Shi, "Binderless Adsorbents with Improved Mass Transfer Properties and Their Use in the Adsorptive Separation of Para-Xylene," pending U.S. Appl. No. 12/165,359.
Priegnitz, James W., "Binderless Adsorbents and Their Use in the Adsorptive Separation of Para-Xylene," pending U.S. Appl. No. 12/165,390.
Cheng, Linda Shi, "Adsorbents with Improved Mass Transfer Properties and Their Use in the Adsorptive Separation of Para-Xylene," pending U.S. Appl. No. 12/165,412.
U.S. Appl. No. 12/165,390, filed Jun. 30, 2008, Priegnitz et al.
U.S. Appl. No. 12/165,359, filed Jun. 30, 2008, Cheng et al.
U.S. Appl. No. 12/165,412, filed Jun. 30, 2008, Cheng et al.
U.S. Appl. No. 12/165,329, filed Jun. 30, 2008, Kulprathipanja et al.
ADS-23 Adsorbent—UOP Technical Data Sheet (2006).
Meta-Xylene Sorbex —UOP Technical Data Sheet (2006).
"KP Selects UOP in South Korea" NPRA 2007 Q&A Technology Forum p. 8, (2007).

* cited by examiner

*Primary Examiner*—Tam M Nguyen
(74) *Attorney, Agent, or Firm*—David J Piasecki

(57) ABSTRACT

Adsorbents and methods for the adsorptive separation of meta-xylene from a mixture containing at least one other $C_8$ aromatic hydrocarbon (e.g., a mixture of ortho-xylene, meta-xylene, para-xylene, and ethylbenzene) are described. Suitable adsorbents comprise sodium zeolite Y having an average crystallite size from about 50 to about 700 nanometers. The adsorbents provide improved separation efficiency, which may be associated with a higher meta-xylene mass transfer rate and/or other beneficial effects. Exemplary desorbents for use in the process may comprise toluene, benzene, or indan.

20 Claims, 1 Drawing Sheet

ADSORBENT AND PROCESS FOR THE SEPARATION OF META-XYLENE FROM AROMATIC HYDROCARBONS

FIELD OF THE INVENTION

The present invention relates to adsorbents and methods for the adsorptive separation of meta-xylene from a mixture containing at least one other $C_8$ alkylaromatic hydrocarbon (e.g., a mixture of ortho-xylene, meta-xylene, para-xylene, and ethylbenzene).

DESCRIPTION OF RELATED ART $C_8$ alkylaromatic hydrocarbons are generally considered to be valuable products, with a high demand for both meta-xylene and para-xylene. Meta-xylene is a feedstock for the manufacture of purified isophthalic acid (PIA). It is also used in insecticides, as an intermediate for higher quality unsaturated polyesters, and as a modifier for polyethylene terephthalate (PET) resins. A major source of meta-xylene is a mixed xylene stream that results from the refining of crude oil.

Particularly, in typical $C_8$ alkylaromatic hydrocarbon formation processes, the reaction product contains a mixture of ethylbenzene, ortho-xylene, meta-xylene, and para-xylene. Therefore, the desired $C_8$ alkylaromatic hydrocarbon isomer must be separated from the mixture. Historically, industry has sought ways to separate para-xylene, traditionally the most desired compound, from the mixture, and numerous patents exist to that end. For example, zeolites X and Y have been used to selectively adsorb para-xylene. See, for example, U.S. Pat. No. 3,903,187, U.S. Pat. No. 4,313,015, U.S. Pat. No. 4,899,017, U.S. Pat. No. 5,171,922, U.S. Pat. No. 5,177,295, U.S. Pat. No. 5,495,061, and U.S. Pat. No. 5,948,950. U.S. Pat. No. 4,940,830 describes a rejective separation of para-xylene from other xylene isomers and ethylbenzene using sodium zeolite Y or a sodium zeolite Y that is ion exchanged with a Groups IB or Group VII element. A gas-phase process using adsorptive separation to recover para-xylene from a mixture of xylenes, with an adsorbent comprising a crystalline molecular sieve having an average crystal size between 0.5 and 20 microns is described in WO 2008/033200.

There have also been proposals to recover meta-xylene, for example from aromatic-rich hydrocarbon mixtures such as naphtha reformates by adsorption in the same manner that para-xylene is now recovered. It has also been suggested to recover meta-xylene from the process streams circulating in xylene isomerization units prior to or after the recovery of other desired xylene isomers. Examples of such proposals, which use fractionation and crystallization, are described in U.S. Pat. No. 3,700,744, U.S. Pat. No. 3,729,523, and U.S. Pat. No. 3,773,846. The use of extractive distillation for meta-xylene recovery is described in U.S. Pat. No. 4,585,526. Overall, the recovery of meta-xylene according to these methods has not been a commercial success and much meta-xylene in these sources is simply converted to other materials such as benzene or para-xylene.

With growing interest in meta-xylene, patents directed to the separation of meta-xylene are becoming more numerous. For example, U.S. Pat. No. 6,137,024 describes a rejective separation of meta-xylene from other xylene isomers using zeolite Beta. US 2007/0038012 describes an absorptive separation of meta-xylene using a faujasite type zeolite. U.S. Pat. No. 5,900,523 and U.S. Pat. No. 5,382,747 describe adsorbing meta-xylene using a sodium- or a sodium- and lithium-exchanged zeolite Y to separate meta-xylene from a mixture of $C_8$ aromatic hydrocarbons including other xylene isomers in the liquid phase. U.S. Pat. No. 4,368,347 describes a rejective separation of meta-xylene using zeolite Y exchanged with potassium.

There remains a need in the art for improved adsorbents and processes for the efficient separation of meta-xylene from a relatively impure mixture of $C_8$ alkylaromatic hydrocarbons.

SUMMARY OF THE INVENTION

The invention relates to adsorbents that selectively adsorb meta-xylene over at least one other $C_8$ alkylaromatic compound present in a mixture. Due to the practical limitations of reaction equilibrium/selectivity, as well as evaporative (distillation) separations, typical mixtures obtained from oil refining processes contain the other xylene isomers, ortho-xylene and para-xylene (in addition to meta-xylene), in varying amounts and usually also contain ethylbenzene. Such mixtures will normally constitute feed streams used in methods associated with the invention.

Accordingly, embodiments of the invention are directed to processes for separating meta-xylene from a relatively impure mixture of one or more $C_8$ alkylaromatic hydrocarbons other than the desired meta-xylene. The mixture is contacted under adsorption conditions with an adsorbent comprising sodium-exchanged zeolite Y. Aspects of the invention are associated with the finding that "nano sodium zeolite Y" (i.e., nano-size zeolite Y crystallites in sodium form and having an average crystallite size below one micron) provides highly favorable performance characteristics when incorporated into adsorbents used in the adsorptive separation of meta-xylene. In particular, the mass transfer rate of meta-xylene into the zeolite pores is significantly greater, relative to sodium zeolite Y synthesized according to conventional methods (and typically having an average crystallite size on the order of 1-3 microns).

This increase in mass transfer rate in turn reduces the amount of adsorbent required to obtain a given flow rate of product (e.g., an extract product stream) from a given feed stream, for any desired set of performance parameters (e.g., meta-xylene purity and recovery). Process economics are therefore improved. Moreover, adsorbents using the "nano sodium zeolite Y" can have greater meta-xylene capacity with comparable or greater meta-xylene/toluene, meta-xylene/ethylbenzene, meta-xylene/para-xylene, and meta-xylene/ortho-xylene selectivities, relative to conventional sodium zeolite Y adsorbents with larger average zeolite crystallite sizes. Other beneficial effects due to the nano-size zeolite Y are believed to result in the observed performance advantages.

Exemplary zeolite crystallite sizes for nano sodium zeolite Y are in the range from about 50 to about 700 nanometers (nm), and are often from about 50 to about 300 nanometers. The nano sodium zeolite Y may be used in solid adsorbents employed in fixed bed, moving bed, or simulated moving bed adsorptive separation processes employing conventional adsorption conditions. Adsorption may be performed in the liquid or gas phase, with liquid phase adsorption conditions normally being favored.

Particular embodiments of the invention thus relate to a process for separating meta-xylene from a mixture comprising at least one other $C_8$ alkylaromatic hydrocarbon, with the mixture normally containing the xylene isomers ortho- and para-xylene as well as ethylbenzene. The process comprises contacting the mixture with an adsorbent comprising sodium zeolite Y having an average zeolite crystallite size as discussed above. Exemplary adsorption temperatures range from about 60° C. to about 250° C., with about 120° C. to about 150° C. being typical for primarily liquid phase operation. Adsorption pressures may range from slightly above atmospheric pressure, for example about 1 barg (15 psig) to about 40 barg (580 psig).

The nano-size zeolite Y used to formulate adsorbents for such adsorptive separations will generally have a molecular silica to alumina ($SiO_2/Al_2O_3$) molar ratio from about 4.0 to about 6.5, corresponding to an atomic Si/Al ratio from about 2.0 to about 3.25. The zeolite is also normally in its sodium form (i.e., nano sodium zeolite Y), having at least 80% and typically at least 95% or substantially all (at least 99%) of its ion-exchangeable sites exchanged with sodium. The sodium-exchanged, nano-size zeolite crystallites may be formulated into larger adsorbent particles by being bound with a suitable binder such as clay, alumina, silica, zirconia, or mixtures of these amorphous materials. The binder is normally present in an amount ranging from about 5% to about 25% by weight, relative to the total adsorbent weight.

The contact between the mixture of $C_8$ alkylaromatic hydrocarbons described above (e.g., as a continuous or batch process feed stream) effects or brings about the adsorption of meta-xylene into the nano sodium zeolite Y pores, in preference to at least one other $C_8$ alkylaromatic hydrocarbon and normally in preference to all of such hydrocarbons present in the mixture. Therefore, an adsorbed phase (i.e., within the zeolite pores) will be selectively enriched in meta-xylene content, relative to that of the mixture of $C_8$ alkylaromatic compounds (e.g., the feed stream). If the mixture contains ortho-xylene, meta-xylene, para-xylene, and ethylbenzene, then meta-xylene will be present in the adsorbed phase, in an enriched amount relative to the mixture, and ortho-xylene, para-xylene, and ethylbenzene will be present in the non-adsorbed phase, in enriched amounts relative to the mixture. The non-adsorbed phase may then be removed from (or flushed) from contact with the adsorbent, for example in a raffinate stream. The adsorbed phase, enriched in meta-xylene, may be separately desorbed from the adsorbent, for example in an extract stream.

A desorbent stream comprising a desorbent such as toluene, benzene, indan, or a mixture thereof may be used for both the flushing and desorption. Aspects of the invention are associated with the particular advantages obtained in processes for the adsorptive separation of meta-xylene using an adsorbent comprising nano sodium zeolite Y and indan as a desorbent. Indan is relatively weak desorbent, compared to other aromatic ring-containing hydrocarbons. Indan therefore allows the adsorbent to exhibit a greater capacity for the desired extract component, namely meta-xylene. The combination of an adsorbent comprising the nano sodium zeolite Y with a desorbent comprising indan not only results in a faster cycle time of operation, but also improves the overall efficiency of separation of the desired meta-xylene.

An exemplary adsorptive separation process utilizing adsorbents discussed above may be performed continuously in a simulated moving bed mode. According to this embodiment, a $C_8$ alkylaromatic hydrocarbon feed stream as described above and the desorbent stream are continuously charged into a fixed bed of the adsorbent, while the extract and raffinate streams are continuously removed from the bed.

During a simulated moving bed mode or other type of adsorptive separation mode, it may be desired to monitor the water content of an outlet stream, such as an extract or raffinate stream, in order to determine the water content or level of hydration of the adsorbent. If necessary, water may be added to an inlet stream, such as a feed stream and/or desorbent stream, either continuously or intermittently, to maintain a desired level of adsorbent hydration (e.g., corresponding to a Loss in Ignition from about 1.0% to about 3.5%). Alternatively, water may be added to obtain an absolute water content in the extract stream and/or raffinate stream, for example, from about 20 ppm by weight to about 120 ppm by weight, corresponding to this adsorbent hydration level or another desired adsorbent hydration level.

These and other aspects and features relating to the present invention are apparent from the following Detailed Description.

DETAILED DESCRIPTION

Figure 1:
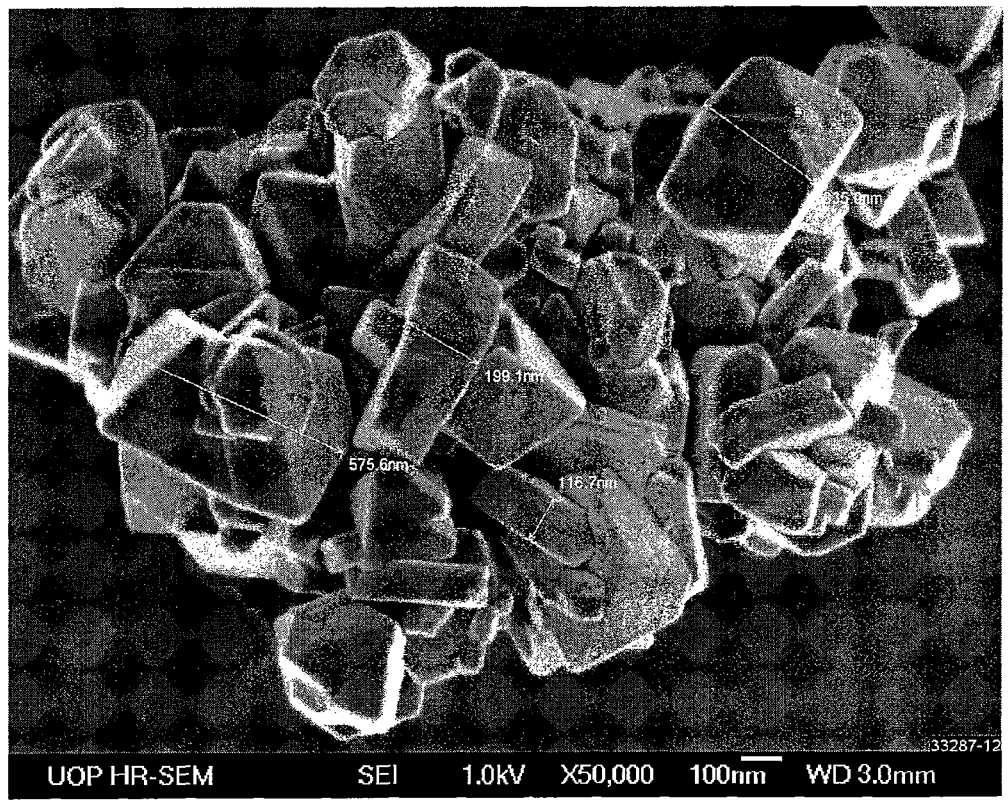
FIG. 1 shows a Scanning Electron Microscopy (SEM) micrograph of nano-size zeolite Y crystallites, prepared as described herein.

As discussed above, the invention relates to the separation of meta-xylene from a mixture comprising at least one other $C_8$ alkylaromatic hydrocarbon. The term separation refers to the recovery of meta-xylene in a stream (e.g., a product stream) or fraction having an enriched meta-xylene content (i.e., a content that is higher than initially present in the mixture). The separation is achieved through contacting the mixture with an adsorbent comprising sodium zeolite Y having an average crystallite size of less than one micron, typically in the range from about 50 to about 700 nanometers, and often in the range from about 50 to about 300 nanometers.

The structure of zeolite Y is described, and further references are provided, in Meier, W. M, et al., *Atlas of Zeolite Structure Types*, 4$^{th}$ Ed., Elsevier: Boston, pp. 62-63 and 104-105 (1996). See also U.S. Pat. No. 4,940,830 and U.S. Pat. No. 3,130,007. The composition and structure of zeolite Y is additionally discussed in Breck, D. W., *Zeolite Molecular Sieves: Structure, Chemistry, and Use*; John Wiley & Sons: New York, pp. 93, 97, and 177 (1974). The framework silica:alumina molar ratio of the zeolite Y is typically between about 4.0:1 and about 6.5:1 and often less than about 5.5:1.

Nano-size zeolite Y having an average crystallite size of less than one micron (e.g., less than about 700 nanometers, less than about 500 nanometers, or less than about 300 nanometers) is synthesized according to the procedures described in application publication US 2007/0224113, incorporated by reference herein in its entirety. Zeolite crystallites refer to individual crystals as opposed to agglomerated crystals which are usually referred to as zeolite particles. The average crystallite size may be determined from Scanning Electron Microscopy (SEM) analysis of zeolite Y crystallites.

In general, the nano-size zeolites which can be synthesized include any of the zeolites having a composition represented by the empirical formula:

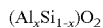
$(Al_xSi_{1-x})O_2$ where Al and Si are framework elements present as tetrahedral oxide units and "x" has a value from greater than 0 to about 0.5. Specific structure types of zeolites which can be prepared include zeolite Y as well as a number of other zeolite structure types including, but not limited to, zeolite X, structure types BEA, FAU, MFI, MEL, MTW, MOR, LTL, LTA, EMT, ERI, FER, MAZ, MEI, TON, and MWW.

One necessary part of the nano-size zeolite synthesis process is an initiator. The initiator is a concentrated, high pH aluminosilicate solution which can be clear or cloudy and has a composition represented by an empirical formula of:

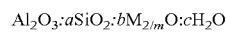
$Al_2O_3:aSiO_2:bM_{2/m}O:cH_2O$ where "a" has a value from about 4 to about 30, "b" has a value from about 4 to about 30, and "c" has a value from about 50 to about 500, "m" is the valence of M and has a value of +1 or +2 and M is a metal selected from the group consisting of alkali metals, alkaline earth metals and mixtures thereof with preferred metals being lithium, sodium, potassium and mixtures thereof. The initiator is prepared by mixing reactive sources of Al, Si and M plus water.

Accordingly, the aluminum sources include but are not limited to, aluminum alkoxides, precipitated alumina, aluminum hydroxide, aluminum salts and aluminum metal. Specific examples of aluminum alkoxides include, but are not limited to aluminum orthosec-butoxide, and aluminum orthoisopropoxide. Sources of silica include but are not limited to tetraethylorthosilicate, fumed silicas, precipitated silicas and colloidal silica. Sources of the M metals include but are not limited to the halide salts, nitrate salts, acetate salts, and hydroxides of the respective alkali or alkaline earth metals. When M is sodium, preferred sources are sodium aluminate and sodium silicate. The sodium aluminate is prepared in situ by combining gibbsite with sodium hydroxide. Once the initiator is formed it is aged at a temperature of about 0° C. to about 100° C. for a time sufficient for the initiator to exhibit the Tyndall effect. Usually the time varies from about 1 hr to about 14 days and preferably from about 12 hours to about 10 days.

A second component of the nano-size zeolite synthesis process is a reaction solution from which the desired zeolite will be synthesized. This solution will have a composition represented by an empirical formula of:

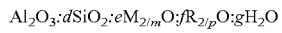

$Al_2O_3 : dSiO_2 : eM_{2/m}O : fR_{2/p}O : gH_2O$ where "d" has a value from about 4 to about 30, "e" has a value from about 4 to about 30, "f" has a value from 0 to about 30 and "g" has a value from about 5 to about 500, "p" is the valence of R and has a value of +1 or +2, R is an organoammonium cation selected from the group consisting of quaternary ammonium ions, protonated amines, protonated diamines, protonated alkanolamines, diquaternary ammonium ions, quaternized alkanolamines and mixtures thereof, the reaction solution formed by combining reactive sources of Al, Si, M and R plus water. The sources of aluminum, silicon and M are as described above, while the sources of R include but are not limited to hydroxide, chloride, bromide, iodide and fluoride compounds. Specific examples include without limitation ethyltrimethylammonium hydroxide (ETMAOH), diethyldimethylammonium hydroxide (DEDMAOH), propylethyldimethylammonium hydroxide (PEDMAOH), trimethylpropylammonium hydroxide, trimethylbutylammonium hydroxide (TMBAOH), tetraethylammonium hydroxide, hexamethonium bromide, tetramethylammonium chloride, N,N,N,N',N',N'-hexamethyl 1,4 butanediammonium hydroxide and methyltriethylammonium hydroxide. The source of R may also be neutral amines, diamines, and alkanolamines. Specific examples are triethanolamine, triethylamine, and N,N,N',N' tetramethyl-1,6-hexanediamine.

A reaction mixture is now formed by mixing the initiator and reaction solution. Usually the initiator is slowly added to the reaction solution and stirred for an additional period of time to ensure homogeneity. The resultant reaction mixture is now charged to an autoclave and reacted under autogenous pressure at a temperature of about 25° C. to about 200° C. for a time of about 1 hr to about 40 days. Reaction can be carried out either with or without stirring. After reaction is complete, the solid zeolite is separated from the reaction mixture by means well known in the art such as filtration or centrifugation, washed with deionized water and dried in air at ambient temperature up to about 100° C.

The exchangeable cations M and R can be exchanged for other desired cations and in the case of R can be removed by heating to provide the hydrogen form of the nano-size zeolites. These zeolites can be used in various hydrocarbon conversion processes or as adsorbents. FIG. 1 provides a Scanning Electron Microscopy (SEM) micrograph of a sample of nano-size zeolite Y crystallites, prepared according to the methods described above. As shown in this image, representative crystallite dimensions or sizes resulting from the synthesis procedure are 575.6 nm, 199.1 nm, 116.7 nm, and 335.0 nm, with an average crystallite size in the ranges discussed above.

The nano-size zeolite prepared as described above, and particularly nano-size zeolite Y, may be in its sodium form or otherwise converted to its sodium form (nano sodium zeolite Y) using known ion exchange techniques. For example, nano-size zeolite Y synthesized with at least some of its ion-exchangeable sites in ammonium ion form may be immersed in a sodium chloride solution (e.g., containing 1-10 wt-% NaCl) under conditions of time and temperature (e.g., about 0.5 to about 10 hours at about 20 to about 125° C.) which can effect substantially complete ion exchange or replacement of ammonium ions with sodium ions. Filtration of the zeolite, removal from the solution, and re-immersion in fresh solution can be repeated multiple times until a desired level of exchange is achieved. Normally, the nano sodium zeolite Y used in adsorbents described herein have at least 95% of their ion-exchangeable sites exchanged with sodium. Generally, no other metal ions occupy ion-exchangeable sites in an amount effective to alter the adsorptive properties of the zeolite.

Optionally, a minor portion of the ion-exchangeable sites (e.g., about 5-15%) of the nano-size zeolite Y may be exchanged with lithium ions. This may be accomplished, for example, starting with nano sodium zeolite Y, prepared as discussed above, and performing an exchange using a lithium ion solution to replace about 5-15 mol-% of the sodium ions with lithium ions.

Typically, the nano sodium zeolite Y crystallites are bound with a suitable binder (e.g., an amorphous inorganic matrix such as clay, alumina, silica, zirconia, or mixtures thereof) into considerably larger adsorbent particles (e.g., in the range of about 16-60 Standard U.S. Mesh size) for use adsorptive separations. A clay comprising both silica and alumina (e.g., minugel clay) is an exemplary material for the non-zeolitic, amorphous binder of the adsorbent, which is present in intimate mixture with the zeolite crystallites. This binder or matrix material may be an adjunct of the manufacturing process for the zeolite (e.g., from the intentionally incomplete purification of the zeolite during its manufacture) or it may be added to the relatively pure zeolite. In either case its usual function of the binder is aid in forming the nano-size zeolite crystallites into hard adsorbent particles, such as extrudates, aggregates, tablets, macrospheres or granules having a desired particle size range.

The zeolite will ordinarily be present in the adsorbent particles in an amount from about 75% to about 95% based on the volatile-free weight of the adsorbent composition. Volatile-free compositions are obtained by calcining the adsorbent, for example, at 900° C.

Those skilled in the art will recognize that the performance of an adsorbent (e.g., in terms of meta-xylene purity and recovery into an extract stream) is influenced by a number of process variables, including operating conditions, feed stream composition, water content, and desorbent type and composition. The optimum adsorbent composition is therefore dependent upon a number of interrelated variables. In general, processes for the adsorptive separation of meta-xylene from a mixture containing at least one other $C_8$ alkylaromatic hydrocarbon, as described herein, can achieve high meta-xylene purity (e.g., at least about 99 wt-% or even at least about 99.5 wt-%) in the extract product stream with a high overall recovery of meta-xylene from the feed stream (e.g., at least about 90%, at least about 92%, or even at least about 95%).

One consideration associated with overall adsorbent performance is its water content, which may be determined from a Loss on Ignition (LOI) test that measures the weight difference obtained by drying a sample of the unused adsorbent at 500° C. under an inert gas purge such as nitrogen for a period of time (e.g., 2 hours) sufficient to achieve a constant weight. The sample is first conditioned at 350° C. for 2 hours. The percentage of weight loss, based on the initial sample weight, is the LOI at 500° C. An LOI from about 1.0% to about 3.5% by weight is generally desired for the adsorbents comprising nano sodium zeolite Y. To monitor the adsorbent LOI during an adsorptive separation process, it may be desired to determine the water content of a suitable outlet stream of such a process, for example the raffinate stream and/or extract stream. Also, the adsorbent LOI may be adjusted or maintained, if desired, through continuous or intermittent addition or injection of water into a suitable inlet stream, for example the feed stream or desorbent stream. According to one exemplary embodiment, the adsorbent LOI is maintained by monitoring the water content in the extract and/or raffinate streams. For example, a representative range of water in either or both of these streams, corresponding to a desirable adsorbent LOI, is from about 20 ppm by weight to about 120 ppm by weight. Often the desired water content in one or both of these outlet streams is from about 40 ppm to about 80 ppm by weight. Water may be added to either the feed stream or the desorbent stream, as discussed above, in continuous or intermittent injections to maintain these measured water levels in the extract stream, raffinate stream, or both.

It is recognized that LOI is an indirect or relative measurement of the adsorbent hydration level (or water content), as other volatile components (e.g., organic materials) are also lost during the analysis. Therefore, the desired adsorbent water content is simply that which corresponds to an LOI from about 1.0% to about 3.5% by weight, measured as described above. If necessary, the absolute amount of water in a zeolitic adsorbent sample can be determined by known analytical methods such as Karl Fischer (ASTM D1364).

Although the adsorptive separation of meta-xylene from other $C_8$ alkylaromatic compounds may be conducted in either the liquid phase or the vapor phase, predominantly liquid-phase operation is normally used. Adsorption conditions can include a temperature range from about 60° C. to about 250° C., and often from about 120° C. to about 150° C. Adsorption conditions can also include a pressure range from about atmospheric to about 600 psig, with pressures from about 1 barg (15 psig) to about 40 barg (580 psig) being typical. Desorption conditions often include substantially the same temperature and pressure as used for adsorption.

Separation of meta-xylene is carried out by contacting a mixture of meta-xylene and at least one other $C_8$ alkylaromatic hydrocarbon with an adsorbent, and under adsorption conditions, as described above. For example, a feed stream comprising the mixture of $C_8$ alkylaromatic hydrocarbons may be contacted with a bed of the adsorbent in order to selectively adsorb, in an adsorbed phase, the meta-xylene, in preference to ortho-xylene, para-xylene, and ethylbenzene.

These other $C_8$ alkylaromatic components of the feed stream may selectively pass through the adsorption zone as a non-adsorbed phase.

Feed streams comprising mixtures of $C_8$ alkylaromatic hydrocarbons can be separated from various refinery process streams (e.g., reformate) including the products of separation units. Such separations are imprecise and the feed is therefore expected to contain limited amounts (e.g., less than 5 mol-%, and often less than 2 mol-%) of other compounds, such as $C_9$ alkylaromatic hydrocarbons. In most instances the feed will be primarily $C_8$ alkylaromatic hydrocarbons and contain a total of less than 10 mol-%, typically less than 5 mol-%, and in some cases less than 1 mol-%, of other types of compounds. In one type of separation process, after the adsorptive capacity of the adsorbent is reached, the feed stream inlet flow to the adsorbent is stopped, and the adsorption zone is then flushed to remove a non-adsorbed phase, initially surrounding the adsorbent, from contact with the adsorbent. The adsorbed phase, enriched in the desired meta-xylene, may be thereafter desorbed from the adsorbent pores by treating the adsorbent with a desorbent, normally comprising a cyclic hydrocarbon (e.g., an aromatic ring-containing hydrocarbon) such as toluene, benzene, indan, or mixtures thereof. The same desorbent is commonly used for both (i) flushing the non-adsorbed phase into a raffinate stream comprising the desorbent and (ii) desorbing the adsorbed phase into an extract stream, also comprising the desorbent. Because the extract stream contains the adsorbed phase, which is enriched in meta-xylene, the extract stream will also be enriched in meta-xylene, relative to the feed stream, when considered on a desorbent-free basis.

As used herein, a "feed stream" is a mixture containing the desired extract component (meta-xylene) and one or more raffinate components to be separated by the adsorptive separation process. A "feed mixture" (i.e., comprising "feed mixture components") therefore comprises the mixture of extract and raffinate components, such as a mixture of xylenes (ortho-xylene, meta-xylene, and para-xylene as discussed above) and ethylbenzene. The feed stream is an inlet stream to the adsorbent (e.g., in the form of one or more adsorbent beds) used in the process. An "extract component" is a compound or class of compounds that is selectively adsorbed by the adsorbent. A "raffinate component" is a compound or class of compounds that is less selectively adsorbed (or selectively rejected). A "desorbent" is generally any material capable of desorbing an extract component from the adsorbent, and a "desorbent stream" is an inlet stream to the adsorbent, which contains desorbent. A "raffinate stream" is an outlet stream from the adsorbent, in which a raffinate component is removed. The composition of the raffinate stream can vary from essentially 100% desorbent to essentially 100% raffinate components, with minor amounts one or more extract components. An "extract stream" is an outlet stream from the adsorbent, in which an extract component is removed. The composition of the extract stream can vary from essentially 100% desorbent to essentially 100% extract components, with minor amounts of one or more raffinate components.

Typically, at least some portion of the extract stream and the raffinate stream are purified (e.g., by distillation) to remove desorbent and thereby produce an extract product stream and a raffinate product stream. The "extract product stream" and "raffinate product stream" refer to products produced by the adsorptive separation process containing, respectively, an extract component and a raffinate component in higher concentration than present in the extract stream and the raffinate stream, respectively, and also in higher concentration than present in the feed stream.

The capacity of the adsorbent for adsorbing a specific volume of an extract component is an important characteristic, as increased capacity makes it possible to reduce the amount of adsorbent (and consequently the cost) needed to separate the extract component for a particular charge rate of feed mixture. Good initial capacity for the extract component, as well as total adsorbent capacity, should be maintained during actual use in an adsorptive separation process over some economically desirable life.

The rate of exchange of an extract component (meta-xylene) with the desorbent can generally be characterized by the width of the peak envelopes at half intensity obtained from plotting the composition of various species in the adsorption zone effluent obtained during a pulse test versus time. The narrower the peak width, the faster the desorption rate. The desorption rate can also be characterized by the distance between the center of the tracer peak envelope and the disappearance of an extract component which has just been desorbed. This distance is time dependent and thus a measure of the volume of desorbent used during this time interval. The tracer is normally a relatively non-adsorbed compound which moves through an adsorbent column faster than the materials to be separated.

The rate at which one species of a mixture moves in and out of the adsorbent can also be reported in terms of a quantity referred to as stage time. Stage time is calculated based upon the half width of a component peak and serves to correct observations otherwise founded on net retention volumes of the individual species. The calculation of stage time has been described in "Principles of Adsorption and Adsorption Processes" by Douglas M. Ruthven, published by John Wiley & Sons, 1984. A shorter stage time does not indicate a component has a shorter residence time in the adsorption zone. Stage times are however an accurate indication of the relative amount of adsorbent required to perform a given separation. Short stage times are therefore desirable in any system destined for commercialization and which therefore involves large investments for the plant, equipment, adsorbent, etc. An excessively high stage time renders a commercial simulated moving bed separation commercially infeasible if there is a practical alternative.

Selectivity ($\beta$), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The selectivity corresponds to the ratio of the two components in the adsorbed phase divided by the ratio of the same two components in the non-adsorbed phase at equilibrium conditions. Selectivity may therefore be calculated from:

$$\text{Selectivity} = (\text{wt-\%}\ C_A/\text{wt-\%}\ D_A)/(\text{wt-\%}\ C_U/\text{wt-\%}\ D_U)$$

where C and D are two components of the feed mixture represented in weight percent and the subscripts A and U represent the adsorbed and non-adsorbed phases, respectively. The equilibrium conditions are determined when the feed passing over a bed of adsorbent does not change composition, in other words, when there is no net transfer of material occurring between the non-adsorbed and adsorbed phases. In the equation above, a selectivity larger than 1.0 indicates preferential adsorption of component C within the adsorbent. Conversely, a selectivity less than 1.0 would indicate that component D is preferentially adsorbed leaving an non-adsorbed phase richer in component C and an adsorbed phase richer in component D.

For a selectivity of two components approaching 1.0, there is no preferential adsorption of one component by the adsorbent with respect to the other (i.e., they are both adsorbed to about the same degree with respect to each other). As selectivity deviates from 1.0, there is an increasingly preferential adsorption by the adsorbent for one component with respect to the other. Selectivity can be expressed not only for one feed stream compound relative to another (e.g., meta-xylene to para-xylene selectivity) but can also be expressed between any feed stream compound and the desorbent (e.g., meta-xylene to toluene selectivity).

While separation of an extract component from a raffinate component is theoretically possible when the adsorbent selectivity for the extract component with respect to the raffinate component is only slightly greater than 1, it is preferred that this selectivity is at least 2 for process economic considerations. Analogous to relative volatility in fractional distillation, the higher the selectivity, the easier the adsorptive separation is to perform. Higher selectivities directionally permit a smaller amount of adsorbent to be used, just as higher relative volatilities require fewer theoretical stages of distillation (and a smaller column) to effect a given distillation separation for a given feed.

The desorbent for an adsorptive separation process must be judiciously selected to satisfy several criteria. The desorbent should ideally displace an extract component from the adsorbent at a reasonable mass flow rate, without itself being so strongly adsorbed as to prevent an extract component from displacing the desorbent in a following adsorption cycle. In terms of the selectivity, it is preferred that the adsorbent be more selective for the extract component with respect to a raffinate component than it is for the desorbent with respect to the raffinate component. Additionally, the desorbent must be compatible with both the adsorbent as well as the feed mixture. In particular, the desorbent should not adversely effect the desired selectivity of the adsorbent for an extract component with respect to a raffinate component. Additionally, the desorbent should be essentially chemically inert with respect to extract and raffinate components, as both the extract stream and the raffinate stream are typically removed from the adsorbent in admixture with desorbent. Any chemical reaction involving desorbent and an extract component or a raffinate component would complicate or possibly prevent product recovery.

A performance parameter to be considered for the desorbent is therefore its rate of exchange for the extract component of the feed or, in other words, the relative rate of desorption of the extract component. This parameter relates directly to the amount of desorbent that must be used in an adsorptive separation process to desorb the extract component from the adsorbent. Faster rates of exchange reduce the amount of desorbent needed and therefore reduce operating costs associated with larger desorbent-containing process streams, including the separation and recycle of desorbent from these streams. A desorbent selectivity of 1 or slightly lower with respect to an extract component helps ensure that all the extract component is desorbed with a reasonable flow rate of desorbent, and also that extract components can displace desorbent in a subsequent adsorption step. As a final consideration, the desorbent should generally be readily available at a favorable cost.

In processes for the adsorptive separation of meta-xylene using an adsorbent comprising a nano sodium zeolite Y as discussed herein, particular performance advantages in this regard are obtained using a desorbent stream comprising indan. The combination of the nano sodium zeolite Y and indan desorbent results in a highly efficient separation due to the increased mass transfer and shorter cycle times associated with the adsorbent, together with the favorable rate of exchange of indan for meta-xylene, leading to the advantages discussed above. The relatively weak adsorption of indan, compared to other aromatic ring-containing adsorbents, results in correspondingly faster meta-xylene desorption (i.e., a sharper desorption peak) and consequently improved meta-xylene separation efficiency. In terms of operation in a simulated moving bed mode as discussed in more detail below, the desorption characteristics of indan result in reduced "tailing" or contamination of the extract stream with components (e.g., ortho-xylene) of the "tail" of the raffinate peak.

Moreover, since both the raffinate stream and the extract stream normally contain desorbent, the desorbent should also be easily separable from the mixture of extract and raffinate components introduced in the feed stream. Without a method of separating desorbent in the extract stream and the raffinate stream, the concentration of an extract component in the extract product and the concentration of a raffinate component in the raffinate product would not be commercially favorable, nor would the desorbent be available for reuse in the process. At least a portion of the desorbent is therefore normally recovered from the extract stream and the raffinate stream of an adsorptive separation process by distillation or evaporation, although other separation methods such as reverse osmosis could also be used alone or in combination with distillation or evaporation. In this regard, the desorbent indan is "heavy" desorbent which is easily separable, as a distillation bottoms product, from the $C_8$ alkylaromatic hydrocarbons in the extract stream and raffinate stream of a meta-xylene adsorptive separation process. The normal boiling point of indan, 176.5° C., is more than 30° C. greater than that of the highest boiling xylene compound (ortho-xylene).

A "pulse test" may be employed to test adsorbents with a particular feed mixture and desorbent to measure such adsorbent properties as adsorptive capacity, selectivity, resolution and exchange rate. The basic pulse test apparatus includes a tubular adsorbent chamber of approximately 70 cubic centimeters (cc) in volume and having inlet and outlet portions at opposite ends of the chamber. The chamber is equipped to allow operation at constant, predetermined temperature and pressure. Quantitative and qualitative analytical equipment such as refractometers, polarimeters and chromatographs can be attached to an outlet line of the chamber and used to detect quantitatively and/or determine qualitatively one or more components in the effluent stream leaving the adsorbent chamber. During a pulse test, the adsorbent is first filled to equilibrium with a particular desorbent by passing the desorbent through the adsorbent chamber. A pulse of the feed mixture, which may be diluted with desorbent, is then injected for a duration of one or more minutes. Desorbent flow is resumed, and the feed mixture components are eluted as in a liquid-solid chromatographic operation. The effluent can be analyzed on-stream or, alternatively, effluent samples can be collected periodically and analyzed separately (off-line) and traces of the envelopes of corresponding component peaks plotted in terms of component concentration versus quantity of effluent.

Information derived from the pulse test can be used to determine adsorbent void volume, retention volume for an extract component or a raffinate component, selectivity for one component with respect to the other, stage time, the resolution between the components, and the rate of desorption of an extract component by the desorbent. The retention volume of an extract component or a raffinate component may be determined from the distance between the center of the peak envelope of an extract component or a raffinate component and the peak envelope of a tracer component or some other known reference point. It is expressed in terms of the volume in cubic centimeters of desorbent pumped during the time interval corresponding to the distance between the peak envelopes.

Retention volumes for good candidate systems fall within a range set by extrapolation to commercial designs. A very small retention volume indicates there is little separation between the two components (i.e., one component is not adsorbed strongly enough). Large extract component retention volumes indicate it is difficult for the desorbent to remove the retained extract component. In terms of the pulse test described above, retention volumes in the range of 30-90 cubic centimeters are normally desired.

Conventional apparatuses employed in static bed fluid-solid contacting may be used in adsorptive separation processes incorporating and adsorbent comprising nano sodium zeolite Y, as described above. The adsorbent may be employed in the form of a single fixed bed which is alternately contacted with the feed stream and desorbent stream. The adsorbent may therefore be used in a single static bed that is alternately subjected to adsorption and desorption steps in a non-continuous (e.g., batch) process. A swing bed mode of operation is also possible, in which multiple beds are periodically used for a given operation or step. Alternatively, a set of two or more static beds may be employed with appropriate piping/valves to allow continual passage of the feed stream through any one of a number of adsorbent beds while the desorbent stream is passed through one or more of the other beds in the set. The flow of the feed stream and desorbent may be either upward or downward through the adsorbent.

A countercurrent moving bed mode of operation provides another potential mode of operation, in which a stationary concentration profile of the feed mixture components can be achieved, allowing for continuous operation with fixed points of feed stream and desorbent stream introduction, as well as extract stream and raffinate stream withdrawal. Countercurrent moving bed or simulated moving bed countercurrent flow systems have a much greater separation efficiency than fixed adsorbent systems and are therefore very often used for commercial-scale adsorptive separations. In a simulated moving bed process, the adsorption and desorption are carried out continuously in a simulated moving bed mode, allowing both continuous production (withdrawal) of an extract stream and a raffinate stream (both outlet streams), as well as the continual use (input) of a feed stream and a desorbent stream (both inlet streams).

The operating principles and step sequence of a simulated moving bed flow system are described in U.S. Pat. No. 2,985,589, U.S. Pat. No. 3,310,486, and U.S. Pat. No. 4,385,993, incorporated by reference herein for their teachings with respect to simulated moving bed flow systems. In such systems, it is the progressive movement of multiple access points along an adsorbent chamber that simulates the movement of adsorbent (opposite the liquid access point movement) contained in one or more chambers. Typically only four of the many (16 to 24 or more) access lines to the chamber(s) are active at any one time and carry: the feed stream, the desorbent stream, the raffinate stream, and the extract stream. Coincident with this simulated movement (e.g., upward movement) of the solid adsorbent is the movement (e.g., downward movement) of fluid occupying the void volume of the packed bed of adsorbent. The circulation of this fluid (e.g., liquid) flow may be maintained using pump. As an active liquid access point moves through a cycle, that is, from the top of the chamber to the bottom, the chamber circulation pump generally provides different flow rates. A programmed flow controller may be provided to set and regulate these flow rates.

The active access points effectively divide the adsorbent chamber into separate zones, each of which has a different function. Three separate operational zones are generally present for the process to take place, although, in some cases, an optional fourth operation zone is used. The zone numbers used in the following description of a simulated moving bed process correspond to those illustrated in U.S. Pat. No. 3,392,113 and U.S. Pat. No. 4,475,954, also incorporated by reference herein with respect to their teachings regarding simulated moving bed operation.

The adsorption zone (zone 1) is defined as the adsorbent located between the inlet feed stream and the outlet raffinate stream. In this zone, the feed mixture contacts the adsorbent, an extract component is adsorbed, and a raffinate stream is withdrawn. The general flow through zone 1 is from the feed stream which passes into the zone to the raffinate stream which passes out of the zone, and the flow in this zone is normally considered to be in a downstream direction when proceeding from the inlet feed stream to the outlet raffinate stream.

Immediately upstream, with respect to fluid flow in zone 1, is the purification zone (zone 2). The purification zone is defined as the adsorbent between the outlet extract stream and the inlet feed stream. The basic operations in this zone are the displacement from the non-selective void volume of the adsorbent of any raffinate component carried into zone 2 and the desorption of any raffinate component adsorbed within the selective pore volume of the adsorbent or adsorbed on the surfaces of the adsorbent particles. Purification is achieved by passing a portion of the extract stream leaving zone 3 into zone 2 at its upstream boundary, the extract outlet stream, to effect the displacement of raffinate components. The flow in zone 2 is in a downstream direction from the extract outlet stream to the feed inlet stream. This material then joins the feed stream and flows through zone 1.

Immediately upstream of zone 2 with respect to the fluid flowing in zone 2 is the desorption zone (zone 3). The desorption zone is defined as the adsorbent between the inlet desorbent stream and the outlet extract stream. The function of the desorbent zone is to allow a desorbent which passes into this zone to displace the extract component which was adsorbed in the adsorbent during a previous contact with the feed mixture in zone 1, in a prior cycle of operation. The flow of fluid in zone 3 is essentially in the same direction as that in zones 1 and 2.

In some instances, an optional buffer zone (zone 4) may be utilized. This zone, defined as the adsorbent between the outlet raffinate stream and the inlet desorbent stream, if used, is located immediately upstream with respect to the fluid flow into zone 3. Zone 4 can be utilized to conserve the amount of desorbent needed for desorption, since a portion of the raffinate stream which is removed from zone 1 can be passed into zone 4 to displace desorbent from that zone out into the desorption zone. Zone 4 will contain enough adsorbent so that raffinate components in the raffinate stream passing from zone 1 into zone 4 can be prevented from passing into zone 3 and thereby contaminating the extract stream withdrawn from zone 3. If a fourth operational zone is not utilized, the raffinate stream passed from zone 1 to zone 4 must be carefully monitored in order that the flow directly from zone 1 to zone 3 can be stopped when there is an appreciable quantity of raffinate components present in the raffinate stream passing from zone 1 into zone 3 so that the extract outlet stream is not contaminated.

A cyclic advancement of the input (feed and desorbent) streams and output (extract and raffinate) streams through one or more fixed beds of adsorbent, to provide a continuous process performed in a simulated moving bed mode, can be accomplished by utilizing a manifold system in which the valves in the manifold are operated in a manner which effects the shifting of the input and output streams thereby providing a flow of fluid with respect to solid adsorbent in a simulated countercurrent manner. Another type of operation which can simulate countercurrent flow of solid adsorbent involves the use of a rotating valve in which the input and output streams are each directed by the valve to one of the many lines connected to the adsorbent chamber and by which the location at which the input feed stream, output extract stream, input desorbent stream, and output raffinate stream enter or leave the chamber are advanced in the same direction along the adsorbent bed. Both the manifold arrangement and rotary disc valve are known in the art. A multiple valve apparatus is described in detail in U.S. Pat. No. 4,434,051. Rotary disc valves which can be utilized in this operation are described in U.S. Pat. No. 3,040,777, U.S. Pat. No. 4,632,149, U.S. Pat. No. 4,614,204, and U.S. Pat. No. 3,422,848. These patents disclose a rotary type valve in which the suitable advancement of the various input and output streams from fixed sources can be achieved without difficulty.

In many instances, one operational zone of a simulated moving bed process will contain a much larger quantity of adsorbent than another operational zone. For instance, in some operations the buffer zone can contain a minor amount of adsorbent compared to the adsorbent present in the adsorption and purification zones. As another example, in instances in which a desorbent is used that easily desorbs the extract component from the adsorbent, a relatively small amount of adsorbent will be needed in the desorption zone compared to the amount of adsorbent needed in the buffer zone, adsorption zone, purification zone or all of these zones. Also, it is not required that the adsorbent be located in a single column or vessel, and often two adsorbent chambers (e.g., each provided with 12 access lines) are used. Additional chambers are also contemplated.

Normally at least a portion of the output extract stream will pass to a separation process such as a fractionation column, in order to recover a portion of the desorbent (e.g., for recycle to the adsorptive separation process as a desorbent recycle stream) and produce a purified extract product stream (e.g., containing a reduced amount of desorbent). Preferably at least a portion of the output raffinate stream will also pass to a separation process, in order to recover another portion of the desorbent (e.g., also for recycle to the adsorptive separation process) and a raffinate product stream (e.g., also containing a reduced concentration of desorbent). In large-scale petrochemical units, essentially all of the desorbent is recovered for reuse. The design of fractional distillation facilities for this recovery will be dependent on the materials being separated, the desorbent composition, etc.

Another type of a simulated moving bed flow system suitable for use in adsorptive separation processes described above is a co-current high efficiency simulated moving bed process described in U.S. Pat. No. 4,402,832 and U.S. Pat. No. 4,478,721, incorporated by reference herein with respect to their teachings of this alternative mode of operation. This process has advantages in terms of energy efficiency and reduced capital costs, in cases where products of slightly lower purity are acceptable to the producer.

The scale of adsorptive separation units for the purification of meta-xylene can vary from those of pilot plant scale (see, for example, U.S. Pat. No. 3,706,812) to commercial scale and can range in produce flow rates from as little as a few milliliters an hour to many hundreds of cubic meters per hour.

Overall, aspects of the invention are directed to the exploitation of the unique properties of nano sodium zeolite Y for use in adsorptive separations, and particularly in commercial simulated moving bed operations. In view of the present disclosure, it will be seen that several advantages may be achieved and other advantageous results may be obtained. Those having skill in the art, with the knowledge gained from the present disclosure, will recognize that various changes could be made in the above adsorbent compositions, and processes using these compositions, without departing from the scope of the present disclosure. The chemical processes, mechanisms, modes of interaction, etc. used to explain theoretical or observed phenomena or results, shall be interpreted as illustrative only and not limiting in any way the scope of the appended claims.

The following examples are set forth as representative of the present invention. These examples are not to be construed as limiting the scope of the invention as these and other equivalent embodiments will be apparent in view of the present disclosure and appended claims.

Example 1

Synthesis of Nano-Size Zeolite Y

A container containing 1784 g of a 50 wt-% NaOH solution was heated and to it there were added 313 g of gibbsite alumina. The container was removed from the heat and to it there were added 2206.6 g of deionized water (DI-H$_2$O) and the sodium aluminate solution cooled to room temperature. In a separate container, 2206.6 g of DI-H$_2$O was added to 6604 g of sodium silicate and while stirring the sodium aluminate solution was added. The resultant initiator was aged overnight at 50° C. The initiator had an empirical formula of:

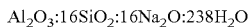

Al$_2$O$_3$:16SiO$_2$:16Na$_2$O:238H$_2$O

A reaction solution was prepared by mixing tetraethylorthosilicate (TEOS) with aluminum tri-sec-butoxide and diethyldimethylammonium (DEDMA) hydroxide to provide a reaction solution having an empirical formula of:

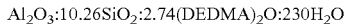

Al$_2$O$_3$:10.26SiO$_2$:2.74(DEDMA)$_2$O:230H$_2$O

The initiator was slowly added to the reaction solution with stirring. The resultant reaction mixture was stirred, transferred to an autoclave where it was reacted at 100° C. for 4 days. After cooling to room temperature, the zeolite Y was separated from the liquid by centrifugation, washed and dried. The zeolite Y was found to have a Si/Al of 3.1 and an average crystallite size of less than 200 nanometers.

Example 2

Preparation of Nano Sodium Zeolite Y by Ion Exchange

The nano-size zeolite Y sample prepared in Example 1, and having ammonium ion exchanged sites, was subjected to ion exchange with sodium ions at a target exchange rate of 1 gram NaCl per gram of zeolite Y, using a 6 wt-% NaCl solution.

In a 2 liter glass beaker, 35 grams of NaCl was dissolved in 548.3 grams of DI-H$_2$O to prepare a sodium ion exchange solution. A 35 gram sample of the nano-size zeolite Y was added to this solution while maintaining mixing on a stir/hot plate. The temperature of the resulting slurry was increased to 75° C. and held for 1-1½ hours with continual mixing. The beaker containing the slurry was then removed from the stir/hot plate, and the slurry was filtered using a Buchner Funnel apparatus with filter paper. The collected filter cake was washed with 1 liter of DI-H$_2$O. The washed filter cake was added to a fresh preparation of sodium ion exchange solution (6 wt-% NaCl), as described above to again form a slurry and perform a second stage of sodium ion exchange, under temperature/time/stirring conditions as described above. A third stage of sodium ion exchange was performed on the nano-size zeolite Y, after which the filter cake obtained was washed three times with DI-H$_2$O, transferred to a drying dish, and dried at 100° C. overnight.

A sample of the resulting nano sodium zeolite Y was submitted for elemental analysis (ICP) and an LOI test as described previously. The sample was found to contain 30.2 wt-% Si, 12.1 wt-% Al, and 9.8 wt-% Na and had an LOI of 8.23%. Based on the elemental analysis, the nano sodium zeolite Y had a framework silica to alumina (SiO$_2$/Al$_2$O$_3$) molar ratio of 4.8 (molar Si/Al ratio=2.4) and a molar Na/Al ratio=0.95.

Example 3

Preparation of Adsorbent Containing Nano Sodium Zeolite Y

A laboratory muller was charged with 86.5 grams of the nano sodium zeolite Y, prepared as described in Example 2. An 8.1 gram portion of minugel clay binder, together with 1.5 grams of crystalline methylcellulose and 2.5 grams DISPEX™ N-40, were also added to the muller. These dry ingredients were mixed in the muller for 20 minutes. A 35.6 gram portion of water was added to the muller, and mixing was continued for 30 minutes. A few grams of water were additionally added to obtain a readily extrudable dough. The dough was then extruded through 0.063" diameter dies with a piston extruder. The formed extrudates were dried at 100° C. for 2 hours. The dried extrudates were calcined by heating to 300° C. in one hour, holding at 300° C. for one hour, heating to 550° C. in one hour, and holding at 550° C. for 2 hours.

Example 4

Comparative Testing of Adsorbents

An adsorbent comprising nano sodium zeolite Y was prepared as described in Examples 1-3 with nano sodium zeolite Y having a framework silica to alumina (SiO$_2$/Al$_2$O$_3$) molar ratio of 5.0 (molar Si/Al ratio=2.5). The adsorbent contained 13.5% clay binder and had an LOI of 2.15 wt-%. A conventional, large crystallite size adsorbent (LCS) (i.e., not containing nano-size crystallites of sodium zeolite Y) was used for reference (comparative) purposes in evaluating performance in the adsorptive separation of meta-xylene. The LCS had a framework silica to alumina (SiO$_2$/Al$_2$O$_3$) molar ratio of 5.0 (molar Si/Al ratio=2.5), contained 13.5% clay binder, and had an LOI of 2.39 wt-%.

A chromatographic separation (breakthrough test) was performed using these adsorbents, initially loaded in a 70 cc column under para-diethylbenzene, on a sample containing a feed mixture of 29.2 wt-% meta-xylene, 13.3 wt-% para-xylene, 14.9 wt-% ortho-xylene, and 13.3 wt-% ethylbenzene. The sample also contained 23.5 wt-% toluene and 5.8 wt-% n-C$_9$ (nonane) tracer. The column temperature was maintained at 100° C. Adsorbent capacity for meta-xylene, total adsorbent capacity, and meta-xylene selectivities, as described above, were determined from the component peaks obtained from the breakthrough analysis. Also, the meta-xylene mass transfer rate was calculated as the "adsorption breakthrough slope," as described in U.S. Pat. No. 4,886,929, incorporated by reference herein with respect to its teaching of the calculation of this quantity (as a volume), which was divided by the volumetric flow rate used to generate the meta-xylene peak, in order to obtain units of time.

Standard pulse tests as described above were also performed using the nano sodium zeolite Y-containing and reference adsorbents, each initially loaded in the 70 cc column under the desorbent toluene. A 2.0 cc feed pulse containing equal quantities of n-$C_9$ (nonane) tracer, ethylbenzene, and each of the three xylene isomers was injected. The column temperature was maintained at 100° C. The meta-xylene selectivities and stage time, as described above, were determined from the component peaks obtained from the pulse test analysis.

Results of the breakthrough and pulse test analysis are shown below in Table 1.

Results of the breakthrough test analyses are shown below in Table 2.

TABLE 1

| Breakthrough Test Results (Toluene vs. Indan Desorbent) | | | | | | |
|---|---|---|---|---|---|---|
| Desorbent | MX Capacity (ml) | Total Capacity (ml) | MX/ Desorbent | MX/ EB | MX/PX | MX/OX |
| Toluene | 4.29 | 10.65 | 1.01 | 1.79 | 3.55 | 1.63 |
| Indan | 5.89 | 11.56 | 2.56 | 1.82 | 3.4 | 1.59 |

The above results show the benefit of using indan desorbent in combination with adsorbent comprising nano sodium zeolite Y, and in particular the more favorable meta-xylene capacity and total adsorbent capacity, resulting from the use of indan desorbent.

The invention claimed is:

TABLE 1

| Breakthrough & Pulse Test Results (LCS vs. Nano Sodium Zeolite Y) | | | | | | | | | |
|---|---|---|---|---|---|---|---|---|---|
| Test | Adsorbent | MX Capacity (ml) | Total Capacity (ml) | MX/Tol | MX/EB | MX/PX | MX/OX | MX Rate Slope (sec) | MX Rate, Stage Time (Sec) |
| Breakthrough | LCS | 5.27 | 11.25 | 1.3 | 5.88 | 2.23 | 2.19 | 722 | |
| Breakthrough | Nano-NaY | 5.28 | 11.5 | 1.3 | 5.76 | 2.37 | 2.33 | 373 | |
| Pulse | LCS | | | | 4 | 1.75 | 1.95 | | 13.64 |
| Pulse | Nano-NaY | | | | 4.16 | 1.94 | 2.07 | | 9.95 |

The above results show that the meta-xylene mass transfer rate is increased considerably, based on the lower stage time and breakthrough slope, for the adsorbent containing nano-size sodium zeolite Y. Moreover, the performance of this adsorbent, in terms of capacity and meta-xylene selectivities relative to ortho-xylene, para-xylene, and ethylbenzene, is comparable or better than the reference zeolite, LCS. The same meta-xylene/toluene selectivity was calculated for both adsorbents tested.

Example 5

Testing of Desorbents, Using Nano Sodium Zeolite Y Adsorbent

An adsorbent comprising nano sodium zeolite Y was prepared as described in Examples 1-3. This adsorbent had a nano sodium zeolite Y framework silica to alumina ($SiO_2$/$Al_2O_3$) molar ratio, clay binder content, and LOI as described in Example 4.

A chromatographic separation (breakthrough test) was performed using these adsorbents, initially loaded in a 70 cc column under para-diethylbenzene, on a sample containing a mixture similar to that described in Example 4 and including toluene desorbent and n-$C_9$ (nonane) tracer. A second breakthrough test was performed, identical in all respects except for the replacement of toluene with indan as the desorbent. The column temperature was maintained at 150° C. in each test. Adsorbent capacity for meta-xylene, total adsorbent capacity, and meta-xylene selectivities, as described above, were determined from the component peaks obtained from the breakthrough analysis.

1. A process for separating meta-xylene from a mixture comprising at least one other $C_8$ alkylaromatic hydrocarbon, the process comprising contacting, under adsorption conditions, the mixture with an adsorbent comprising sodium zeolite Y having an average crystallite size from about 50 to about 700 nanometers to selectively adsorb meta-xylene from the mixture.

2. The process of claim 1, wherein the average crystallite size is from about 50 to about 300 nanometers.

3. The process of claim 1, wherein the adsorption conditions include an adsorption temperature from about 60° C. to about 250° C.

4. The process of claim 1, wherein the adsorption conditions include an adsorption pressure from about 1 barg (15 psig) to about 40 barg (580 psig).

5. The process of claim 1, wherein the adsorbent has a water content corresponding to a Loss on Ignition from about 1.0% to about 3.5% by weight.

6. The process of claim 1, wherein the sodium zeolite Y has a $SiO_2$/$Al_2O_3$ molar ratio from about 4.0 to about 6.5.

7. The process of claim 1, wherein the adsorbent further comprises a binder.

8. The process of claim 7, wherein the binder comprises an amorphous material selected from the group consisting of clay, alumina, silica, zirconia, and mixtures thereof.

9. The process of claim 8, wherein the binder is present in an amount from about 5% to about 25% by weight, relative to the adsorbent.

10. The process of claim 1, wherein the sodium zeolite Y has at least 95% of its ion-exchangeable sites exchanged with sodium.

11. The process of claim 1, wherein the mixture comprises ortho-xylene, meta-xylene, para-xylene, and ethylbenzene.

12. The process of claim 11, wherein contacting the mixture with the adsorbent effects adsorption of meta-xylene, present in an adsorbed phase, in preference to ortho-xylene, para-xylene, and ethylbenzene, present in a non-adsorbed phase.

13. The process of claim 12, further comprising flushing the non-adsorbed phase from contact with the adsorbent.

14. The process of claim 13, further comprising desorbing meta-xylene in the adsorbed phase from the adsorbent.

15. The process of claim 14, wherein meta-xylene in the adsorbed phase is desorbed into an extract stream comprising a desorbent and the non-adsorbed phase is flushed into a raffinate stream comprising the desorbent.

16. The process of claim 15, wherein the desorbent comprises an aromatic ring-containing compound selected from the group consisting of toluene, benzene, indan, and mixtures thereof.

17. The process of claim 15, wherein the process is performed in a simulated moving bed mode, wherein a feed stream and a desorbent stream are charged into one or more vessels comprising the adsorbent, the feed stream comprising the mixture comprising ortho-xylene, meta-xylene, para-xylene, and ethylbenzene, and the desorbent stream comprising the desorbent, and wherein the extract stream and the raffinate stream are removed from the bed of the adsorbent.

18. The process of claim 17 further comprising adding water to either the feed stream or the desorbent stream to obtain a water content of the sodium zeolite Y corresponding to a Loss on Ignition from about 1.0% to about 3.5% by weight.

19. The process of claim 17, wherein water is added to either or both of the feed stream and the desorbent stream to obtain a water content in the extract or raffinate stream from about 20 ppm by weight to about 120 ppm by weight.

20. The process of claim 17, wherein the desorbent is indan.

* * * * *